United States Patent [19]

Ruszkay

[11] Patent Number: 5,202,463
[45] Date of Patent: Apr. 13, 1993

[54] PROCESS FOR THE PREPARATION OF A GLYCOL ETHER ESTER

[75] Inventor: Jude T. Ruszkay, Coatesville, Pa.

[73] Assignee: ARCO Chemical Technology, L.P., Wilmington, Del.

[21] Appl. No.: 757,399

[22] Filed: Sep. 10, 1991

[51] Int. Cl.$^5$ .................. C07C 67/48; B01D 3/34
[52] U.S. Cl. ...................... 560/248; 560/70; 560/240; 560/263; 203/69; 203/62
[58] Field of Search ............ 560/240, 70, 248, 263; 203/69, 62

[56] References Cited

U.S. PATENT DOCUMENTS

| | | | |
|---|---|---|---|
| 3,700,726 | 10/1972 | Johnson et al. | 260/491 |
| 4,314,947 | 2/1982 | Hohenschutz et al. | 260/410 |
| 4,370,491 | 1/1983 | Bott et al. | 560/234 |
| 4,544,453 | 10/1985 | Gupta | 203/44 |

OTHER PUBLICATIONS

CRC Handbook of Chemistry and Physics, 57th edition (1976) p. D-30.
Kirk–Othmer Encyclopedia of Chemical Technology, 3rd ed., vol. 9, Wiley and Sons, 1980, "Esterification," pp. 291–310.

Primary Examiner—Jose' G. Dees
Assistant Examiner—Keith MacMillan
Attorney, Agent, or Firm—Jonathan L. Schuchardt

[57] ABSTRACT

An improved process for preparing and purifying glycol ether esters is disclosed. An azeotroping agent is included at a sufficiently low level to allow removal of the water of reaction, but also permit removal of by-products from esterification in the low-boiling component.

20 Claims, 1 Drawing Sheet

PROCESS FOR THE PREPARATION OF A GLYCOL ETHER ESTER

FIELD OF THE INVENTION

The invention relates to glycol ether ester synthesis and purification. In particular, the invention is a process in which a glycol ether ester is prepared and distilled in the presence of an azeotroping agent capable of concentrating various reaction by-products in a low-boiling component that can be separated from unreacted carboxylic acid and glycol ether components.

BACKGROUND OF THE INVENTION

Esterification of glycol ethers with carboxylic acids to prepare glycol ether esters is well known. The equilibrium reaction is typically performed in the presence of an acid catalyst. Water generated in the reaction is usually removed as a low-boiling component as the reaction mixture is distilled. Removal of water helps to drive the esterification toward completion. Azeotroping agents are commonly used to assist in water removal. Relatively nonvolatile glycol ether esters are often recovered by fractionation from unreacted carboxylic acid and glycol ether components, which are usually more volatile. The latter are then recycled to the reactor.

In a conventional glycol ether ester synthesis, the glycol ether and carboxylic acid, usually acetic acid, are fed to a reactor and partially converted (30-50%) to glycol ether ester and water. The reactor effluent is fed to a distillation column, and the products are separated. Water is removed overhead with the aid of an azeotroping agent. Without the azeotroping agent, significant amounts of acetic acid are removed overhead with the aqueous phase. Water and azeotroping agent are separated using an overhead phase separator, and the organic phase is returned to the column. Unreacted glycol ether and acetic acid are removed as a side stream from the column, and the glycol ether acetate product is recovered from the bottom of the column.

Unfortunately, acid-catalyzed esterification with many glycol ethers is complicated by numerous side reactions, such as ether hydrolysis and cyclization. The by-products formed in these side reactions complicate purification. The boiling points of these undesired materials are often close to the boiling points of the glycol ether and acetic acid. Conventional schemes designed to recycle unreacted acetic acid and glycol ether will also recycle these by-products. The concentration of by-products in the reactor is initially low, but because the by-products are recycled, their concentration in the reactor increases as a function of time, and eventually forces a shutdown of the unit.

An obvious solution to the problem is to fractionally distill the side stream containing glycol ether, acetic acid, and by-products. Unfortunately, some of the by-products often boil at a temperature between the boiling point of acetic acid and the glycol ether, so two additional distillation columns are required, adding cost and inconvenience.

It is therefore an object of the invention to find a way to remove by-products from the esterification reactor effluent. Another object of the invention is to remove the by-products in the overhead stream without overhead loss of glycol ether or carboxylic acid.

SUMMARY OF THE INVENTION

The invention is an improved process for preparing and purifying a glycol ether ester. The process comprises: (a) reacting a glycol ether with a carboxylic acid to form a product mixture containing a glycol ether ester, water, unreacted glycol ether, unreacted carboxylic acid, and various by-products; (b) separating the product mixture by a first distillation into three components: a low-boiling component that includes water, a medium-boiling component that includes unreacted glycol ether and unreacted carboxylic acid, and a high-boiling component that includes the glycol ether ester; (c) introducing at a controlled rate during said first distillation step an azeotroping agent in an amount effective to (i) concentrate the by-products, water, and the azeotroping agent in the low-boiling component, and (ii) concentrate the unreacted carboxylic acid and unreacted glycol ether in the medium-boiling component; and (d) isolating the glycol ether ester.

I have unexpectedly discovered that the by-products can be successfully removed by carefully controlling the amount of azeotroping agent in the distillation column feed. The by-products can be removed overhead without loss of carboxylic acid.

DETAILED DESCRIPTION OF THE INVENTION

Figure 1:
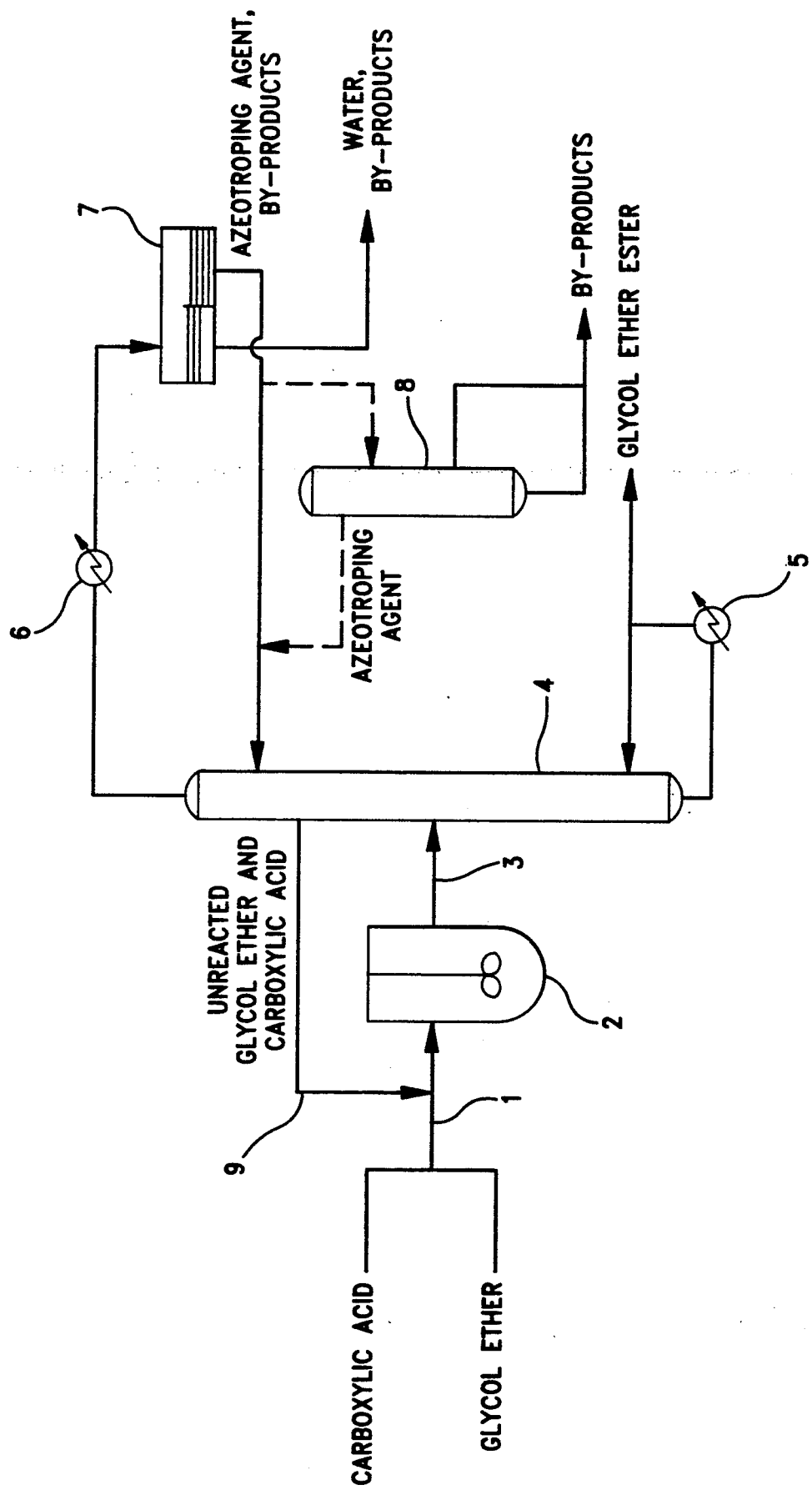
FIG. 1 illustrates the process of the invention. Carboxylic acid and glycol ether are fed into a reactor (2). The reactor effluent is transferred to a first distillation column (4), in which the reaction products are fractionated Unreacted glycol ether and carboxylic acid are recycled to the reactor through a recycle loop (9). The light products, which include water, by-products, and an azeotroping agent, are removed recovered as a high-boiling product.

Esterification of glycol ethers with carboxylic acids is complicated by side reactions not possible with ordinary aliphatic alcohols. If no azeotroping agent is used, by-products generated in the reaction form an azeotrope with some of the water of reaction, and so the by-products can be removed overhead. The level of by-products is usually too low to permit removal of all of the water of reaction in this way. When most of the by-products have been removed, the remaining water and unreacted carboxylic acid will distill overhead. Thus, in the absence of an azeotroping agent, large amounts of carboxylic acid are lost in the overhead distillate.

In conventional processes, sufficient azeotroping agent is recycled to the top of the distillation column to form a binary, two-phase azeotrope with the water generated in the reaction. When glycol ethers are used as reactants, however, only traces of the by-products formed are removed by this method because formation of a water/by-product azeotrope is suppressed by inclusion of the added azeotroping agent. Most of the by-products are recycled to the reactor with unreacted acid and glycol ether.

I have discovered that by including in the distillation column a relatively small amount of an azeotroping agent such as methyl isobutyl ketone, the concentration of by-products in the overhead stream is significantly increased. Surprisingly, removal of the by-products overhead is accomplished without concurrent loss of carboxylic acid or glycol ether reactants in the overhead stream. The key is to add enough of the azeotroping agent to allow removal of water, but not so much as to suppress the formation of the by-product/water azeotrope.

The concentration of the azeotroping agent in the distillation mixture is important. The amount of azeotroping agent present must be that which is effective to concentrate the by-products in the low-boiling component. At the same time, the amount of azeotroping agent used must be effective to concentrate the unreacted glycol ether and carboxylic acid in the medium-boiling component; i.e., the amount of unreacted acid or glycol ether in the overhead fraction is minimized. Preferably, the weight ratio of azeotroping agent to by-products is within the range of about 0.01/1 to about 1/1. More preferred is the range from about 0.05/1 to about 0.5/1.

As shown in FIG. 1, the overhead stream from the first distillation process is separated into two phases. The phase containing by-products and water is purged from the system. The other phase, which contains azeotroping agent and by-products, is returned to the first distillation column either as overhead reflux, as shown in the Figure, or is combined with the reactor effluent in the column feed line (3). Alternatively, the azeotroping agent/by-product mixture is separated in a second distillation column (8), and pure azeotroping agent is refluxed to the first distillation column (4) (as is illustrated) or is mixed with the reactor effluent (3).

The process of the invention is most advantageously used to prepare glycol ether esters from glycol ethers that can form cyclic 5- or 6-membered ether by-products in the presence of an acid catalyst. Thus, the process is especially well suited for use with monoalkyl and monoaryl ethers of diethylene glycol, dipropylene glycol, triethylene glycol, tripropylene glycol, 1,4-butanediol, 1,5-pentanediol, 3-methyl-1,5-pentanediol, and the like.

Carboxylic acids useful in the process of the invention are monocarboxylic acids and halogenated monocarboxylic acids having from 1 to 10 carbons atoms. Suitable carboxylic acids include, but are not limited to, formic acid, acetic acid, chloroacetic acid, propionic acid, n-butyric acid, isobutyric acid, bromoacetic acid, trimethylacetic acid, and the like. Acetic acid is preferred.

The azeotroping agent useful in the process of the invention is any compound capable of: (1) improving separation of water and the carboxylic acid, (2) co-distilling overhead with water, (3) separating substantially from water following distillation, and (4) allowing water removal without suppressing the by-product/water azeotrope.

Representative azeotroping agents include, but are not limited to, aliphatic hydrocarbons, halogenated aliphatic hydrocarbons, aliphatic ketones, aromatic hydrocarbons, and the like. Preferred azeotroping agents are aliphatic ketones. Particularly preferred is methyl isobutyl ketone.

The process of the invention may be performed batchwise, semi-continuously, or continuously, as desired. In a batch process, for example, the esterification is typically performed in a reaction vessel, and the product is refluxed in the presence of the azeotroping agent until water and by-products are removed overhead. Continuous addition of azeotroping agent to the reboiler during water removal helps to maintain the desired ratio of azeotroping agent to by-products. Part of the top phase of the overhead distillate is advantageously recycled such that the desired overhead temperature is maintained.

In a typical continuous process, esterification occurs as streams of glycol ether and carboxylic acid are co-fed through a hot reaction zone, and the product stream is sent to a distillation column for separation. Continuous addition of azeotroping agent to the column feed or the overhead decanter maintains the desired ratio of azeotroping agent to by-products.

The temperature at which the glycol ether and carboxylic acid are reacted varies depending on the identity of the reactants. Typically, the esterification is performed at a temperature greater than about 50° C. At lower temperatures, reaction rates are ordinarily too slow to be useful.

The esterification reaction mixture is fractionally distilled using equipment and methods that are well known to those skilled in the art. The only requirement is that the distillation be effective to substantially separate the product mixture into three components: a low-boiling component that includes water, a medium-boiling component that includes unreacted glycol ether and unreacted carboxylic acid, and a high-boiling component that includes the glycol ether ester.

As noted earlier, the process of the invention is particularly suitable for preparing and purifying glycol ether esters from glycol ethers that can form 5- or 6-membered cyclic ethers in the presence of an acid catalyst. The synthesis of dipropylene glycol methyl ether acetate (DPMAc) is illustrative. When dipropylene glycol methyl ether (DPM) and acetic acid are reacted in the presence of an acid catalyst, numerous by-products are generated from ether hydrolysis and cyclization reactions, including 2,6-dimethyl-1,4-dioxane, 2,5-dimethyl-1,4-dioxane, propylene glycol methyl ether (PM), and propylene glycol methyl ether acetate (PMAc):

Cyclization:

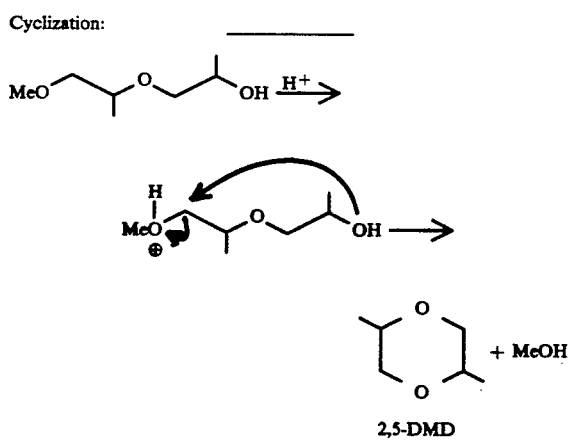

Ether hydrolysis:

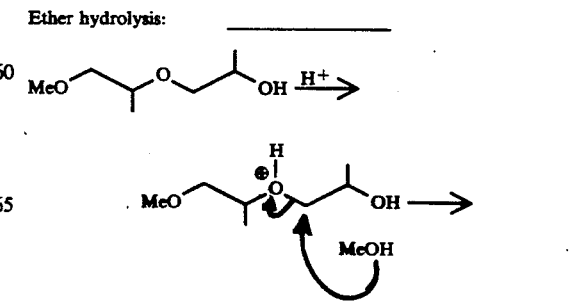

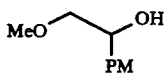

The amount of by-products generated is about 0.5 to 1.5 weight percent. Unfortunately, these by-products have boiling points between those of acetic acid and dipropylene glycol methyl ether. Recycle of the unreacted starting materials from the column to the reactor concentrates the by-products in the reactor, eventually requiring a shutdown.

By adding small amounts of methyl isobutyl ketone (MIBK) (azeotroping agent) into the distillation column feed, the by-products (dimethyl dioxanes, PM, and PMAc) can be removed overhead without loss of acetic acid. The amount of MIBK needed is typically as little as 10% by weight compared with the amount of by-products generated.

The following examples merely illustrate the invention. Those skilled in the art will recognize numerous variations and modifications that are within the scope of the claims.

Sample sources

The samples used for the distillation experiments described below were actual reactor effluents obtained from a plant-scale or pilot-scale esterification process in which dipropylene glycol methyl ether (DPM) was reacted with acetic acid in the presence of an acid catalyst to produce dipropylene glycol methyl ether acetate (DPMAc).

Sample 1 was a pilot-scale reactor effluent that contained no MIBK. This sample was drawn directly from the reactor since there was no recycle loop in the pilot-scale unit.

Sample 3 was a plant sample drawn from the reactant recycle stream in which unreacted DPM and acetic acid were separated from the esterified product in a distillation column and were returned to the esterification reactor. The weight ratio of MIBK to by-products present in this sample was about 0.1/1.

Sample 2 was generated by spiking enough MIBK into Sample 3 to give a MIBK/by-product weight ratio of about 3/1.

Distillation Experiments

Distillation experiments were performed batchwise on a laboratory scale using the samples described above as the initial mixtures. A two-liter two-neck round-bottom flask was equipped with a thermometer and packed column. The top of the column included a reflux splitter. The splitter was equipped with a thermometer, a timer for adjusting the reflux ratio, and a distillate take-off means. Above the splitter was a cold water-cooled condenser equipped at the top with an inlet for maintaining an atmosphere of nitrogen or for evacuating the system. Distillate was removed to a graduated overhead receiver, which could be used to monitor the volume of top and bottom distillate phases, and to drain off the distillate when desired.

Distillations were performed at both atmospheric and reduced pressure. A vacuum pump was used for distillations at reduced pressure, with pressure adjusted by way of an atmospheric bleed valve. The reflux splitter/timer system was used to control the reflux rate. Overhead and pot samples were periodically collected, weighed, and analyzed by gas chromatography. Water concentration was determined by Karl Fisher titration.

The results of the batch distillation experiments appear in Tables 1-3. Table 1 gives the compositions of the initial mixtures and indicates the amounts of water, by-products (propylene glycol methyl ether, propylene glycol methyl ether acetate, dimethyl dioxanes), and MIBK removed overhead as revealed by gas chromatographic analysis of an initial overhead distillate sample.

With no MIBK initially present (Comparative Example 1), distillation of only 1.5 wt. % of the initial mixture removes 62 wt. % of the by-products and 11 wt. % of the water, which apparently form an azeotrope and codistill. With about 10 wt. % MIBK initially present (Comparative Example 2), distillation of about 10 wt. % of the mixture removes 36 wt. % of the water and 87 wt. % of the MIBK, but only 2 wt. % of the by-products. With about 0.5 wt. % of MIBK in the pot (Example 3), distillation of about 3 wt. % of the mixture removes 11 wt. % of the water, 81 wt. % of the MIBK, and 23 wt. % of the by-products.

Table 2 summarizes the compositions of the initial overhead distillate samples. The samples from Comparative Example 1 contain mostly by-products and water, while those of Comparative Example 2 are mostly MIBK and water with only traces of by-products. The samples from Example 3 contain a mixture of water, MIBK, and by-products.

The success of the distillation is measured based on how effectively both water and by-products are removed overhead without a concurrent loss of acetic acid.

As shown in Table 3, distillation with no MIBK initially present is effective for by-product removal, but only 48 wt. % of the water is removed before acetic acid begins to distill overhead. The remaining water is removed only at the expense of a 16 wt. % overhead loss of acetic acid. By-product removal is substantial (79 wt. %), but is completely suppressed once acetic acid begins to distill.

In Comparative Example 2, water removal is essentially complete at the acetic acid breakthrough point (see Table 3), even though the amount of MIBK used is substantially less than the theoretical amount (3 parts MIBK:1 part water) typically used. Unfortunately, 66 wt. % of the by-products remain in the pot.

The most satisfactory balance of water and by-product removal is achieved when a relatively small amount (0.5 wt. %) of MIBK is initially present in the pot (Example 3). At the acetic acid breakthrough point, 59 wt. % of the by-products and 87 wt. % of the water have been removed. The remaining water can be removed with only a 2 wt. % loss of acetic acid.

Based on the results from these three batch distillation experiments, we can predict with reasonable accuracy the expected results from a continuous distillation process.

Substantial losses of acetic acid are expected from continuous distillation in the absence of an azeotroping agent. The concentration of by-products generated is not sufficient to remove all of the water of reaction via a water/by-product azeotrope. Removal of all of the water would require acetic acid loss. The results from Comparative Example 1 and a plant trial are consistent with this prediction.

In a typical continuous industrial process, MIBK is refluxed at a 3:1 MIBK/water ratio to permit removal of all of the water of reaction. Under these conditions, we predict that by-product removal would be essentially nil, and in fact, this is observed in the plant. With enough MIBK present, the water/by-product azeotrope is suppressed, so by-products are not removed. This is confirmed in Comparative Example 2. The initial overhead distillate samples contained almost no by-products. The by-products only appeared in the overhead sample when the concentration of MIBK in the distillation pot became depleted. As shown in Table 3, 34 wt. % of the by-products were ultimately removed in the batch distillation. In a continuous process, however, in which the MIBK concentration is maintained at a 3:1 MIBK/water ratio, it is expected that the by-products would remain almost completely in the pot.

Based on the results from Example 3, we conclude that removal of both by-products and water in a continuous operation will only be possible if the concentration of MIBK at the top of the column is kept sufficiently low. Proper control of the MIBK concentration allows adequate removal of both water and by-products while minimizing overhead loss of acetic acid.

TABLE 1

PURIFICATION OF DIPROPYLENE GLYCOL METHYL ETHER ACETATE

| EXAMPLE # | C-1 | C-2 | 3 |
|---|---|---|---|
| Composition of Initial Mixture (wt. %) | | | |
| Lights | 0.41 | 0 | 0 |
| MIBK | 0 | 9.6 | 0.54 |
| Water | 3.2 | 6.0 | 6.6 |
| Dimethyl dioxanes* | 0.32 | 0.34 | 0.37 |
| PM* | 0.16 | 2.1 | 2.3 |
| PMAc* | 0.21 | 1.8 | 2.0 |
| Acetic acid | 16 | 14 | 16 |
| Heavies | 80 | 66 | 73 |
| Ratio of MIBK/by-products in feed | 0 | 3 | 0.1 |
| Amount of Initial Mixture (g) | 1200 | 1375 | 1204 |
| Initial Overhead Distillate Sample | | | |
| Amount collected (g) | 18.6 | 143 | 34.3 |
| Wt. % of Initial Mixture Collected as Overhead Distillate | 1.5 | 10.4 | 2.8 |
| Wt. % of total water removed | 11 | 36 | 11 |
| Wt. % of by-products removed | 62 | 2 | 23 |
| Wt. % of MIBK removed | — | 87 | 81 |

*By-products
MIBK = methyl isobutyl ketone
PM = propylene glycol methyl ether
PMAc = propylene glycol methyl ether acetate
DPM = dipropylene glycol methyl ether

TABLE 2

PURIFICATION OF DIPROPYLENE GLYCOL METHYL ETHER ACETATE

| Composition of Initial Overhead Distillate Sample | EXAMPLE # | | |
|---|---|---|---|
| | C-1 | C-2 | 3 |
| Top phase | | | |
| MIBK | 0 | 98 | 15 |
| Water | 9.4 | 2 | 14 |
| Dimethyl dioxanes* | 31 | 0.3 | 13 |
| PM* | 40 | 0 | 17 |
| PMAc* | 20 | 0 | 30 |
| DPM | 0 | 0 | 9.2 |
| Acetic acid | 0 | 0 | 0 |
| Bottom phase | | | |
| MIBK | 0 | 2.5 | 2.6 |
| Water | 71 | 98 | 58 |
| Dimethyl dioxanes* | 6.7 | 0 | 5.4 |
| PM* | 7.9 | 0 | 15 |
| PMAc* | 6.4 | 0 | 11 |
| DPM | 0 | 0 | 6.4 |

TABLE 2-continued

PURIFICATION OF DIPROPYLENE GLYCOL METHYL ETHER ACETATE

| Composition of Initial Overhead Distillate Sample | EXAMPLE # | | |
|---|---|---|---|
| | C-1 | C-2 | 3 |
| Acetic acid | 0 | 0 | 0 |

*By-products
MIBK = methyl isobutyl ketone
PM = propylene glycol methyl ether
PMAc = propylene glycol methyl ether acetate
DPM = dipropylene glycol methyl ether

TABLE 3

PURIFICATION OF DIPROPYLENE GLYCOL METHYL ETHER ACETATE

| EXAMPLE # | C-1 | C-2 | 3 |
|---|---|---|---|
| Wt. % of Products Removed at Acetic Acid Break-through Point | | | |
| Water | 48 | 100 | 87 |
| By-products | 79 | 34 | 59 |
| MIBK | — | 100 | 100 |
| Wt. % of Product Removed at 100% Water Removal | | | |
| Acetic acid (loss) | 16 | 0 | 2 |
| By-products | 79 | 34 | 59 |

*By-products
MIBK = methyl isobutyl ketone
PM = propylene glycolmethyl ether
PMAc = propylene glycolmethyl ether acetate
DPM = dipropylene glycol methyl ether

I claim:

1. An improved process for preparing and purifying a glycol ether ester, said process comprising:
   (a) reacting a glycol ether with a carboxylic acid to form a product mixture containing a glycol ether ester, water, unreacted glycol ether, unreached carboxylic acid, and various by-products;
   (b) separating the product mixture by a first distillation into three components: a low-boiling component that includes water; a medium-boiling component that includes unreacted glycol ether and unreacted carboxylic acid; and a high-boiling component that includes the glycol ether ester;
   (c) introducing at a controlled rate during said first distillation step an azeotroping agent in an amount effective to (i) concentrate the by-products, water, and the azeotroping agent in the low-boiling component, and (ii) concentrate the unreacted carboxylic acid and unreacted glycol ether in the medium-boiling component; and
   (d) isolating the purified glycol ether ester; wherein the glycol ether can form a cyclic 5- or 6-membered ether in the presence of an acid catalyst.

2. The process of claim 1 wherein the medium-boiling component, which contains unreacted glycol ether and unreacted carboxylic acid, is continuously recycled to the reactor during the first distillation step.

3. The process of claim 1 wherein:
   (a) the low-boiling component is removed from the first distillation;
   (b) said low-boiling component is separate into an aqueous phase that includes water and by-products, and an organic phase that includes the azeotroping agent and by-products; and
   (c) said organic phase is then returned to the first distillation.

4. The process of claim 3 wherein the organic phase is transferred to a second distillation column to separate the azeotroping agent from the by-products, and then only the azeotroping agent is returned to the first distillation.

5. The process of claim 1 wherein the glycol ether is selected from the group consisting of $C_1$–$C_6$ alkyl and aryl ethers of diethylene glycol, triethylene glycol, dipropylene glycol, and tripropylene glycol.

6. The process of claim 1 wherein the carboxylic acid is selected from the group consisting of acetic acid and propionic acid.

7. The process of claim 1 wherein the azeotroping agent is selected from the group consisting of aliphatic ketones, and aliphatic and aromatic hydrocarbons.

8. The process of claim 1 wherein the amount of azeotroping agent used is sufficient to maintain the weight ratio of azeotroping agent/by-products in the low-boiling component within the range of about 0.05 to 0.5.

9. An improved process for preparing and purifying a glycol ether ester, said process comprising:
  (a) reacting a glycol ether selected from the group consisting of $C_1$–$C_6$ alkyl and aryl ethers of diethylene glycol, triethylene glycol, dipropylene glycol, and tripropylene glycol, with a carboxylic acid selected from the group consisting of acetic acid and propionic acid, to form a product mixture containing a glycol ether ester, water, unreacted glycol ether, unreacted carboxylic acid, and various by-products;
  (b) separating the product mixture by a first distillation into three components: a low-boiling component that includes water; a medium-boiling component that includes unreacted glycol ether and unreacted carboxylic acid; and a high-boiling component that includes the glycol ether ester;
  (c) introducing at a controlled rate during said distillation step an azeotroping agent selected from the group consisting of aliphatic ketones, and aromatic and aliphatic hydrocarbons, in an amount effective to (i) concentrate the by-products, water, and the azeotroping agent in the low-boiling component, and (ii) concentrate the unreacted carboxylic acid and unreacted glycol ether in the medium-boiling component; and
  (d) isolating the purified glycol ether ester.

10. The process of claim 9 wherein the medium-boiling component, which contains unreacted glycol ether and unreacted carboxylic acid, is continuously recycled to the reactor during the first distillation step.

11. The process of claim 9 wherein:
  (a) the low-boiling component is removed from the first distillation;
  (b) said low-boiling component is separated into an aqueous phase that includes water and by-products, and an organic phase that includes the azeotroping agent and by-products; and
  (c) said organic phase is then returned to the first distillation.

12. The process of claim 11 wherein the organic phase is transferred to a second distillation column to separate the azeotroping agent from the by-products, and then only the azeotroping agent is returned to the first distillation.

13. The process of claim 9 wherein the amount of azeotroping agent used is sufficient to maintain the weight ratio of azeotroping agent/by-products in the low-boiling component within the range of about 0.05 to 0.5.

14. The process of claim 9 wherein the glycol ether is dipropylene glycol, the carboxylic acid is acetic acid, and the azeotroping agent is methyl isobutyl ketone.

15. An improved process for preparing and purifying dipropylene glycol methyl ether acetate (DPMAc), said process comprising:
  (a) reacting dipropylene glycol methyl ether (DPM) with acetic acid to form a product mixture containing DPMAc, water, unreacted DPM, unreacted acetic acid, and various by-products, said by-products including dimethyldioxanes, propylene glycol methyl ether, and propylene glycol methyl ether acetate;
  (b) separating the product mixture by a first distillation into three components: a low-boiling component that includes water; a medium-boiling component that includes unreacted DPM and unreacted acetic acid; and a high-boiling component that includes DPMAc;
  (c) introducing at a controlled rate during said distillation step methyl isobutyl ketone in an amount effective to (i) concentrate the by-products, water, and the methyl isobutyl ketone in the low-boiling component, and (ii) concentrate the unreacted acetic acid and unreacted DPM in the medium-boiling component; and
  (d) isolating the purified DPMAc.

16. The process of claim 15 wherein the medium-boiling component, which contains unreacted DPM and unreacted acetic acid, is continuously recycled to the reactor during the first distillation step.

17. The process of claim 15 wherein the amount of methyl isobutyl ketone used is sufficient to maintain the weight ratio of methyl isobutyl ketone/by-products in the low-boiling component within the range of about 0.05 to 0.5.

18. The process of claim 15 wherein:
  (a) the low-boiling component is removed from the first distillation;
  (b) said low-boiling component is separated into an aqueous phase that includes water and by-products, and an organic phase that includes methyl isobutyl ketone and by-products; and
  (c) said organic phase is then returned to the first distillation.

19. The process of claim 18 wherein the organic phase is transferred to a second distillation column to separate methyl isobutyl ketone from the by-products, and then only the methyl isobutyl ketone is returned to the first distillation.

20. The process of claim 18 wherein organic phase is returned to the first distillation at a rate sufficient to maintain the overhead temperature within the range of about 190°–210° F. at atmospheric pressure.

* * * * *